(12) United States Patent
Misaka et al.

(10) Patent No.: US 10,458,775 B2
(45) Date of Patent: Oct. 29, 2019

(54) HARDENED LAYER DEPTH MEASURING APPARATUS

(71) Applicants: NETUREN CO., LTD., Tokyo (JP); OITA UNIVERSITY, Oita (JP)

(72) Inventors: Yoshitaka Misaka, Tokyo (JP); Kazuhiro Kawasaki, Tokyo (JP); Kenta Sakurai, Tokyo (JP); Yuji Gotoh, Oita (JP)

(73) Assignees: NETUREN CO., LTD., Tokyo (JP); OITA UNIVERSITY, Oita (JP)

( * ) Notice: Subject to any disclaimer, the term of this patent is extended or adjusted under 35 U.S.C. 154(b) by 13 days.

(21) Appl. No.: 15/554,319

(22) PCT Filed: Mar. 2, 2016

(86) PCT No.: PCT/JP2016/001142
§ 371 (c)(1),
(2) Date: Aug. 29, 2017

(87) PCT Pub. No.: WO2016/143307
PCT Pub. Date: Sep. 15, 2016

(65) Prior Publication Data
US 2018/0051975 A1   Feb. 22, 2018

(30) Foreign Application Priority Data
Mar. 6, 2015   (JP) .................. 2015-045307

(51) Int. Cl.
*G01B 7/26* (2006.01)
*G01N 27/72* (2006.01)
*G01B 7/06* (2006.01)

(52) U.S. Cl.
CPC ............... *G01B 7/26* (2013.01); *G01B 7/105* (2013.01); *G01N 27/72* (2013.01)

(58) Field of Classification Search
CPC .......... G01B 7/26; G01B 7/105; G01N 27/72
See application file for complete search history.

(56) References Cited

U.S. PATENT DOCUMENTS

| 4,006,406 A | 2/1977 | Rodicker |
| 4,634,976 A * | 1/1987 | Tiitto .................. G01N 27/72 |
| | | 324/209 |

(Continued)

FOREIGN PATENT DOCUMENTS

| EP | 2 360 467 | 8/2011 |
| FR | 2 902 521 | 12/2007 |

(Continued)

OTHER PUBLICATIONS

International Search Report dated Jun. 14, 2016 in International Application No. PCT/JP2016/001142.

(Continued)

*Primary Examiner* — Daniel R Miller
(74) *Attorney, Agent, or Firm* — Wenderoth, Lind & Ponack, L.L.P.

(57) ABSTRACT

An apparatus is provided to measure a depth of a hardened layer formed at a surface layer of a quenched workpiece. The apparatus includes an exciting coil configured to generate a magnetic flux to magnetize the workpiece and a detecting coil configured to detect the magnetic flux generated by the exciting coil. The exciting coil has a U-shaped excitation core portion and an excitation coil portion wound on the excitation core portion. The excitation core portion is arranged such that distal ends of magnetic poles of the excitation core portion face the workpiece. The detecting coil has a detection core portion and a detection coil wound on the detection core portion. The detection core portion is arranged between the magnetic poles of the excitation core portion and along a surface of the workpiece.

9 Claims, 8 Drawing Sheets

(56) References Cited

U.S. PATENT DOCUMENTS

| | | |
|---|---|---|
| 5,565,773 A | 10/1996 | Inaguma et al. |
| 2011/0062953 A1 | 3/2011 | Yamamoto et al. |
| 2011/0199081 A1* | 8/2011 | Masuda ............... G01N 27/725 |
| | | 324/258 |
| 2013/0300405 A1 | 11/2013 | Gotoh et al. |

FOREIGN PATENT DOCUMENTS

| | | |
|---|---|---|
| GB | 1 255 179 | 12/1971 |
| JP | 49-135670 | 12/1974 |
| JP | 05-264508 | 10/1993 |
| JP | 2010-230354 | 10/2010 |
| JP | 2010-243174 | 10/2010 |
| WO | 2009/119529 | 10/2009 |
| WO | 2012/057224 | 5/2012 |

OTHER PUBLICATIONS

Written Opinion of the International Searching Authority dated Jun. 14, 2016 in International Application No. PCT/JP2016/001142.

\* cited by examiner

[Fig. 1A]
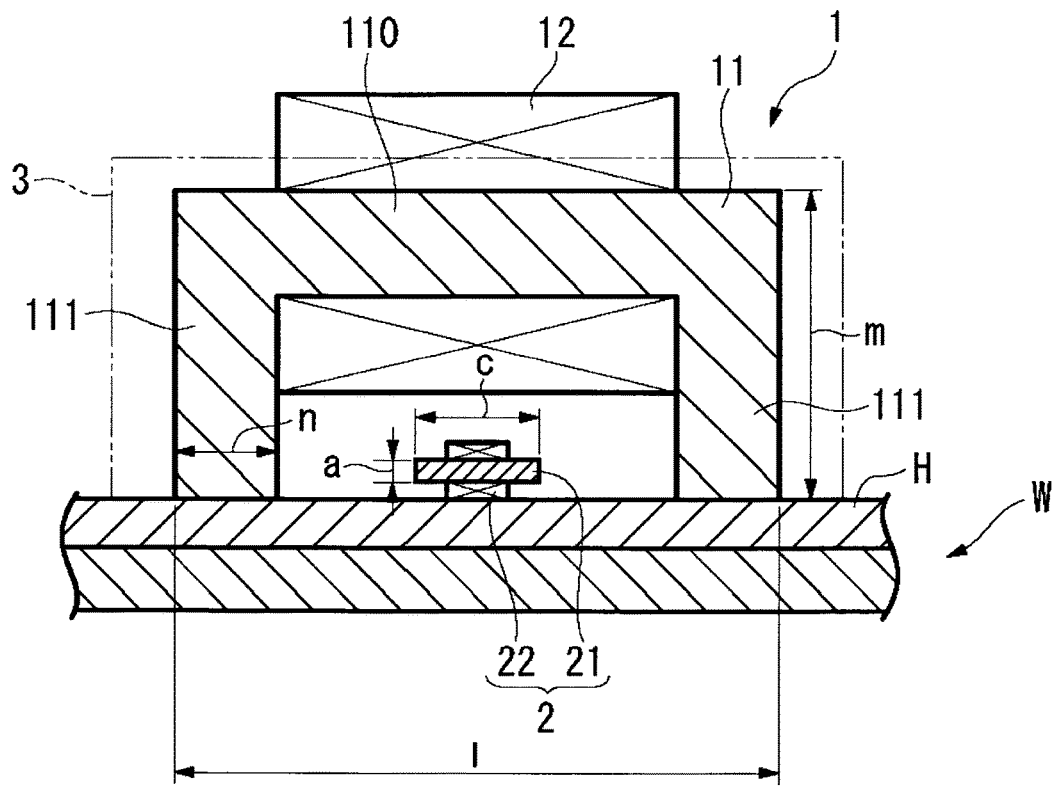
[Fig. 1B]
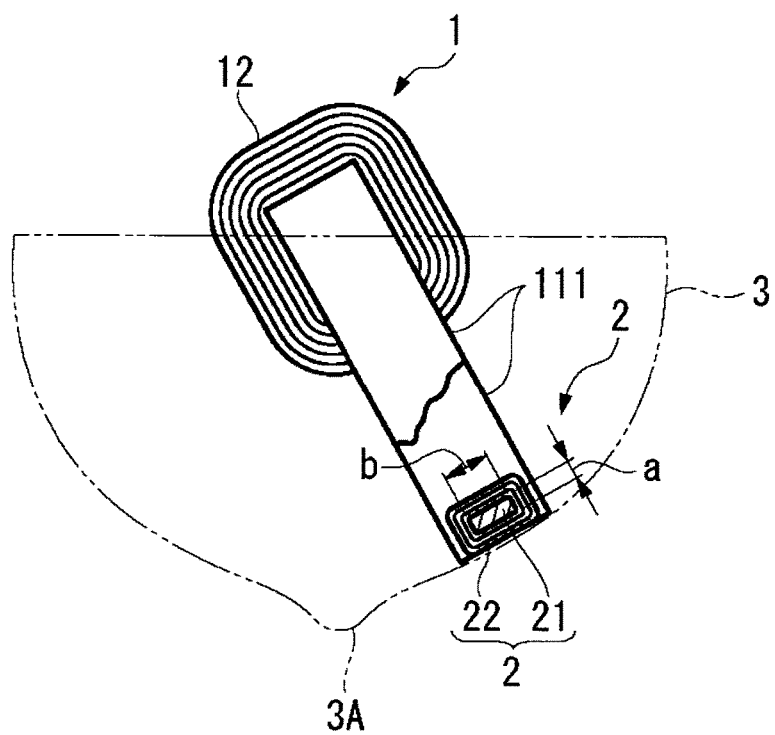

[Fig. 2A]
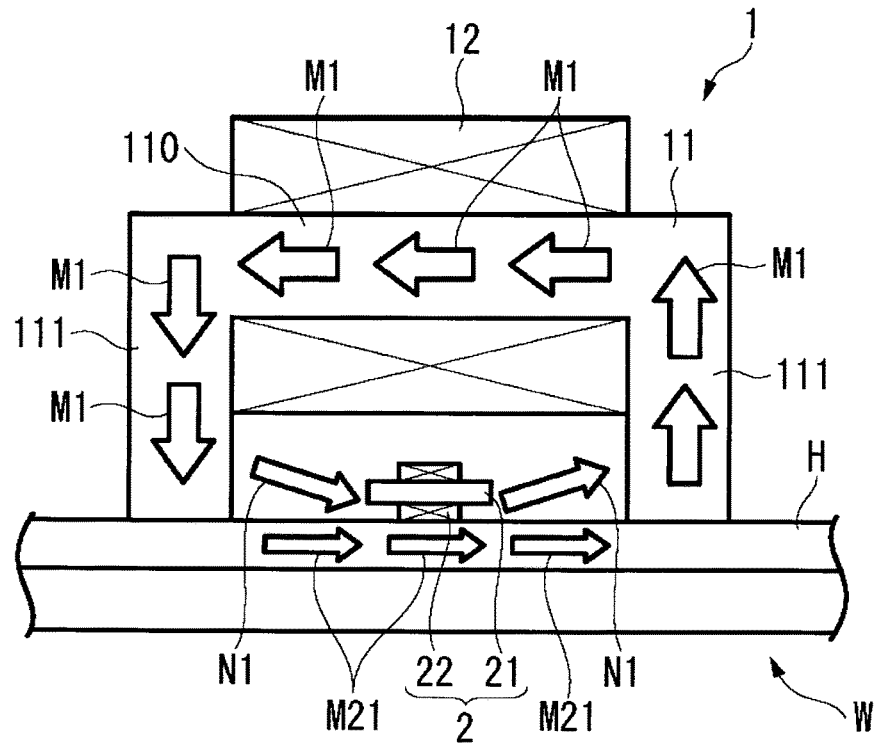
[Fig. 2B]
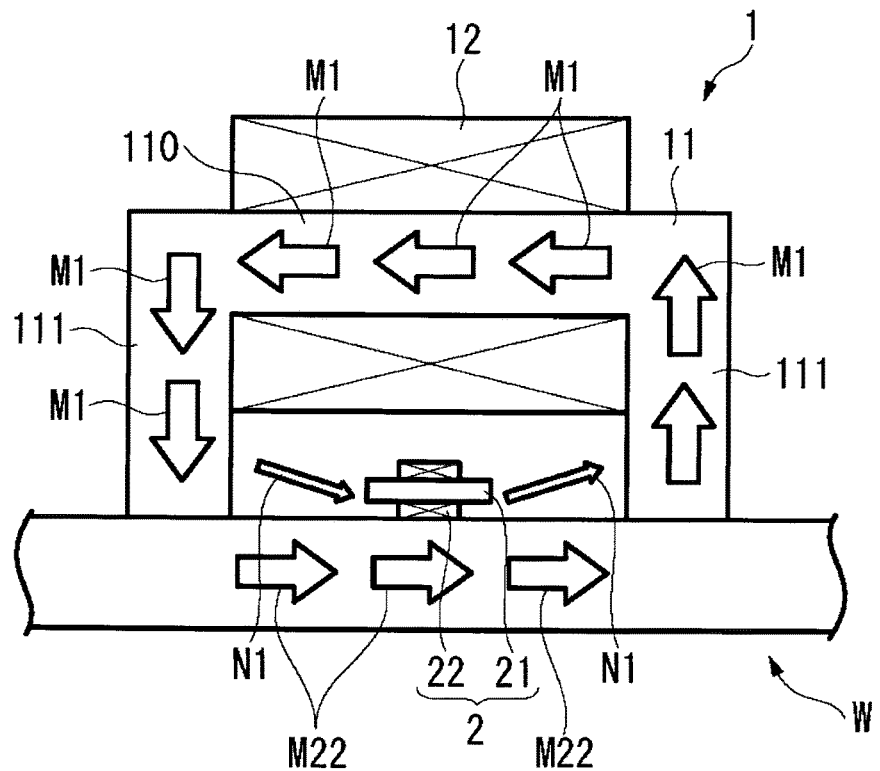

[Fig. 3A]
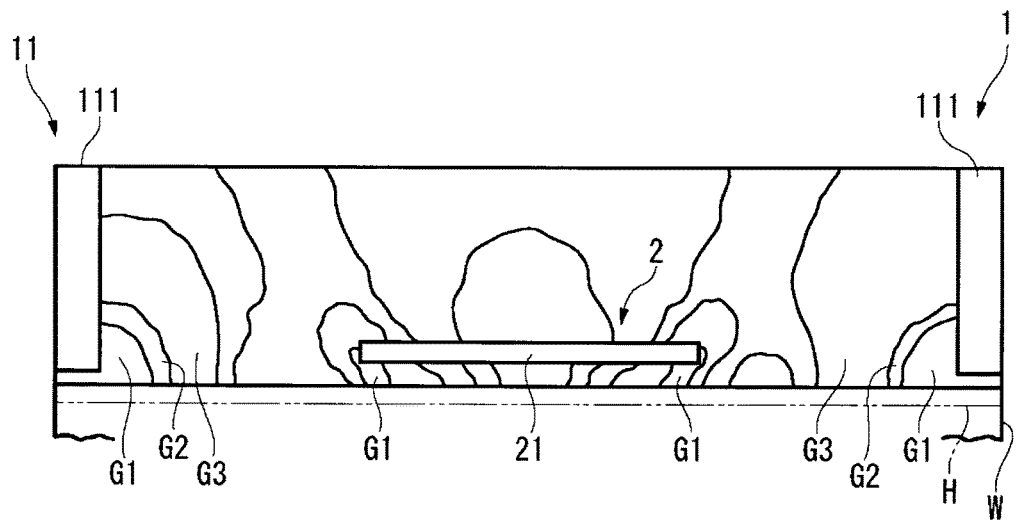
[Fig. 3B]
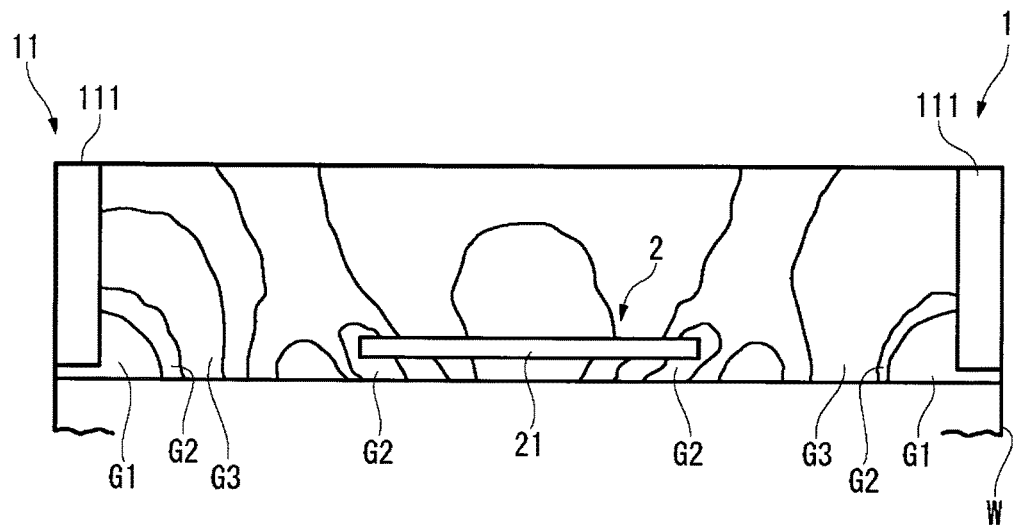

[Fig. 4B]
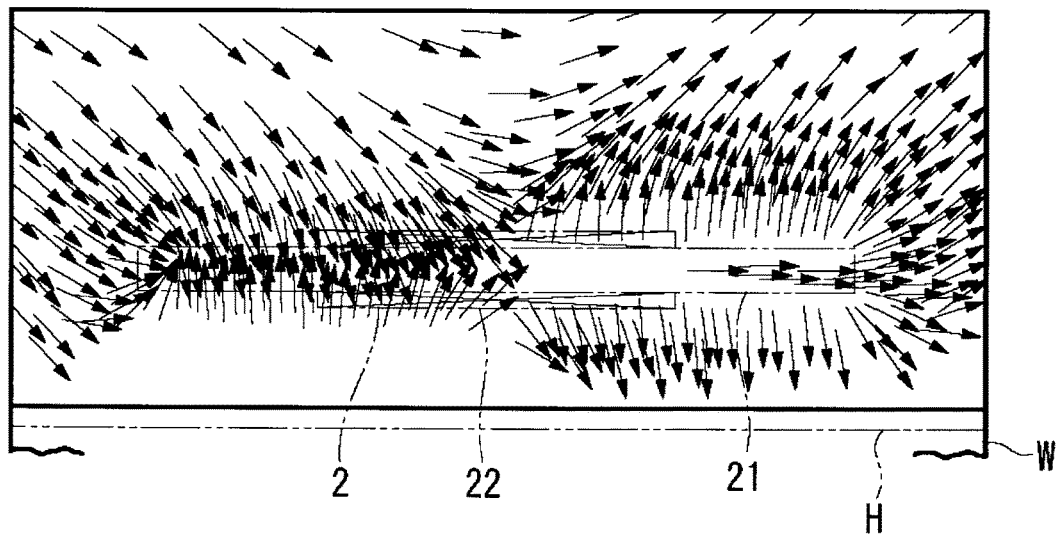
[Fig. 4A]
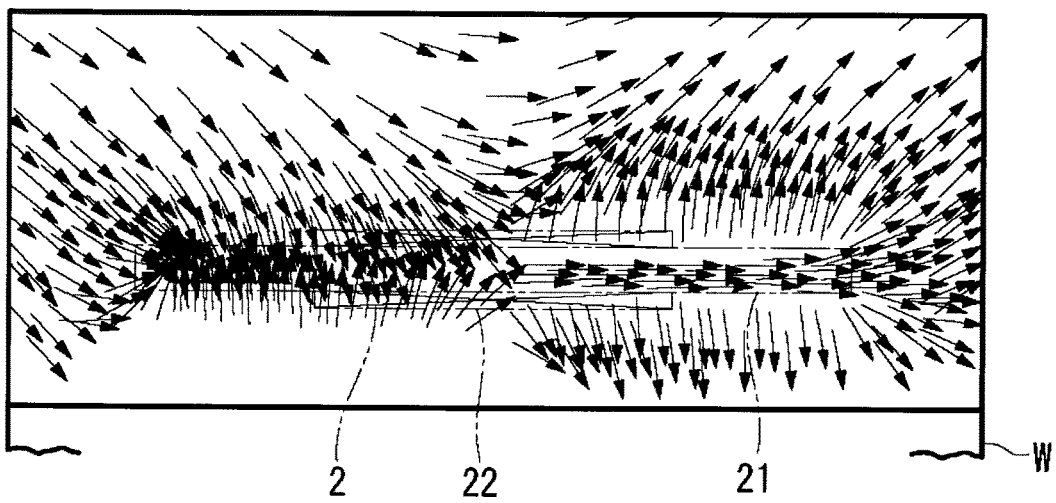

[Fig. 5]
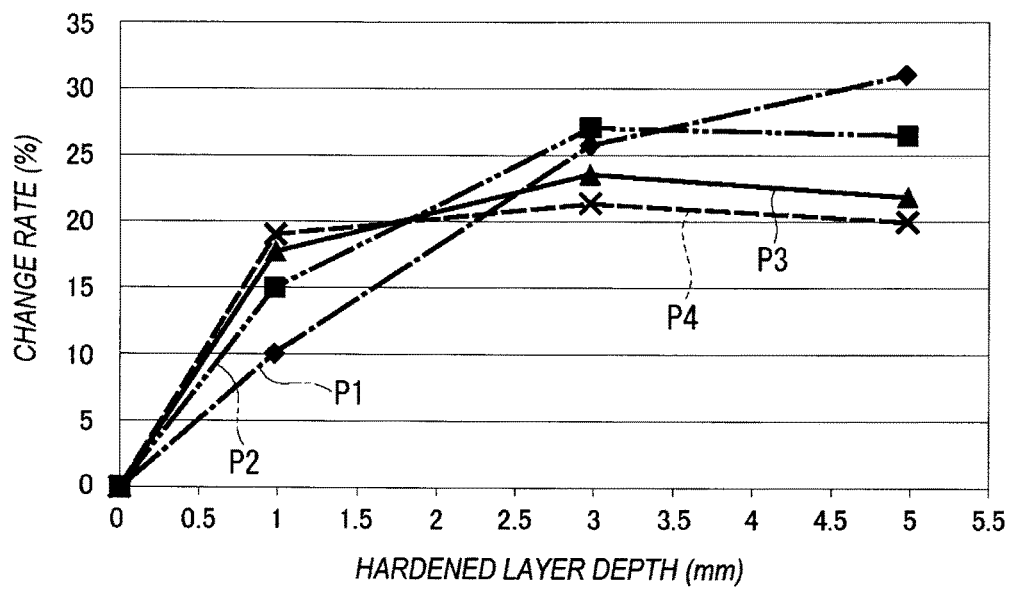
[Fig. 6]
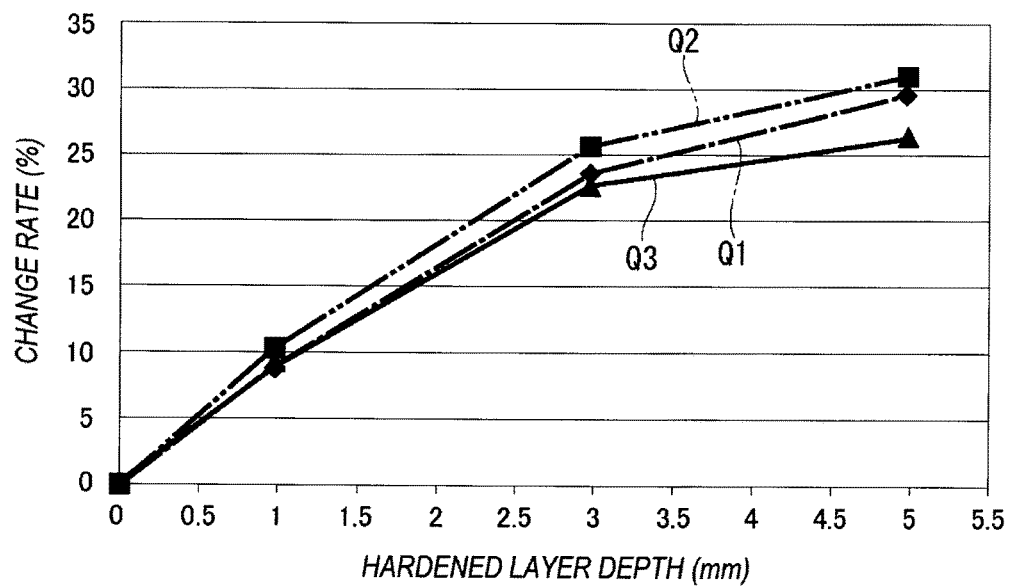

[Fig. 7]
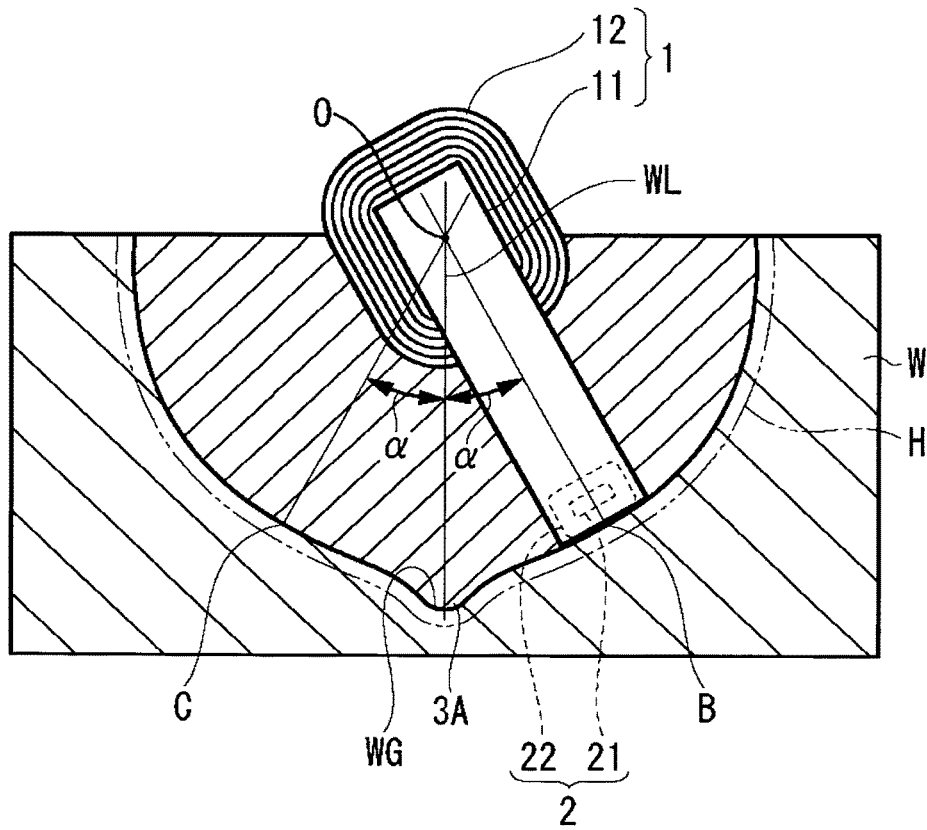
[Fig. 8]
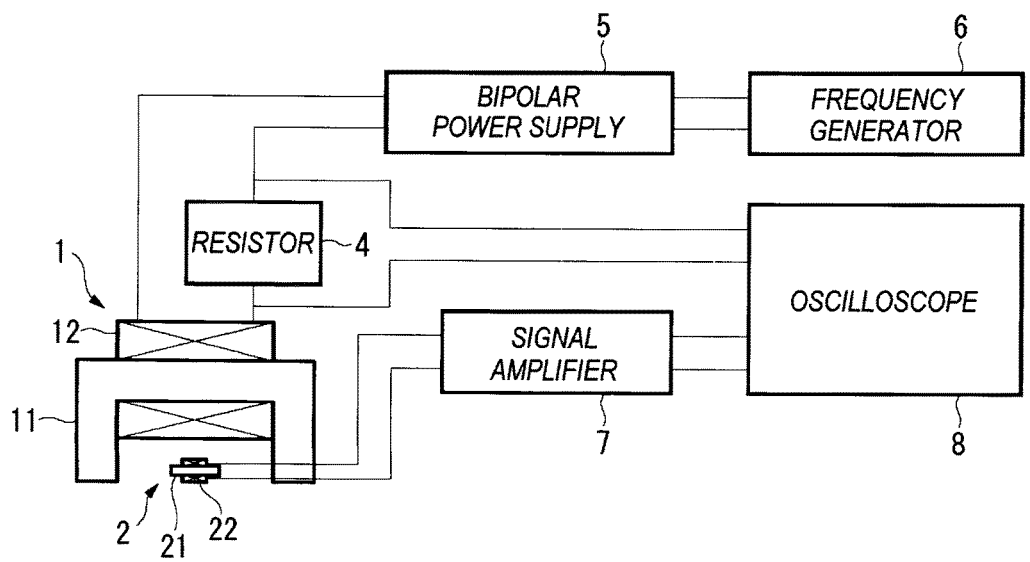

[Fig. 9]
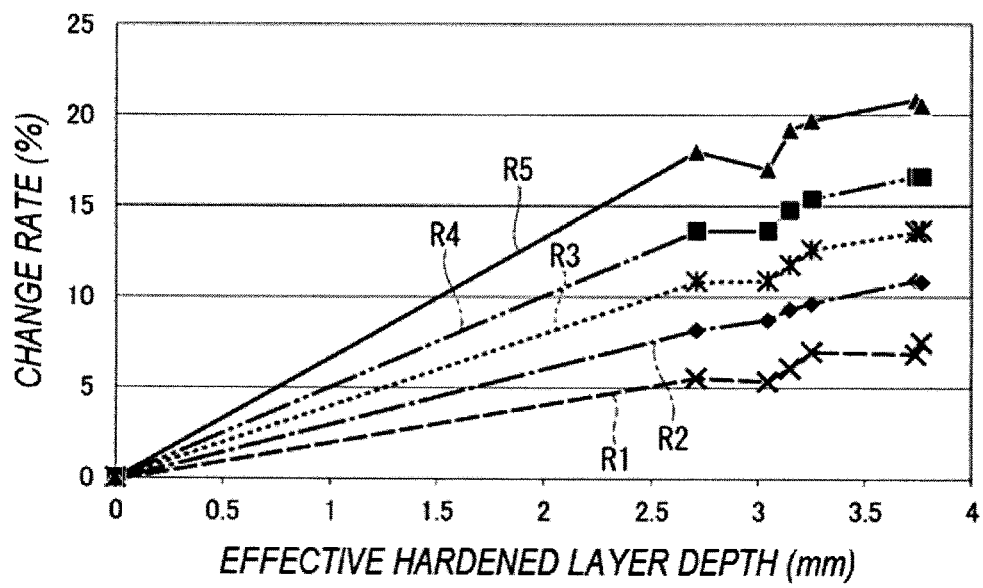
[Fig. 10]
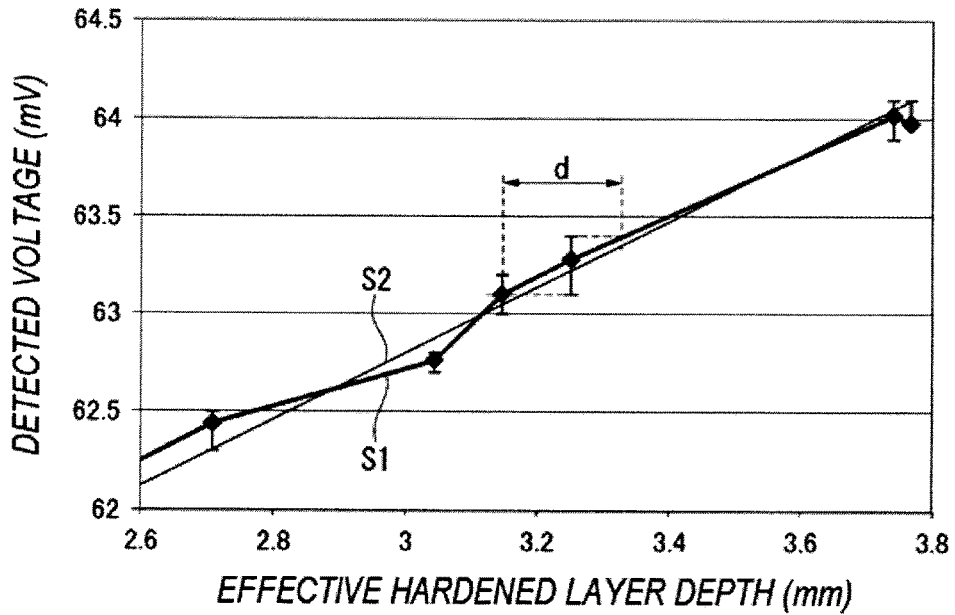

[Fig. 11]
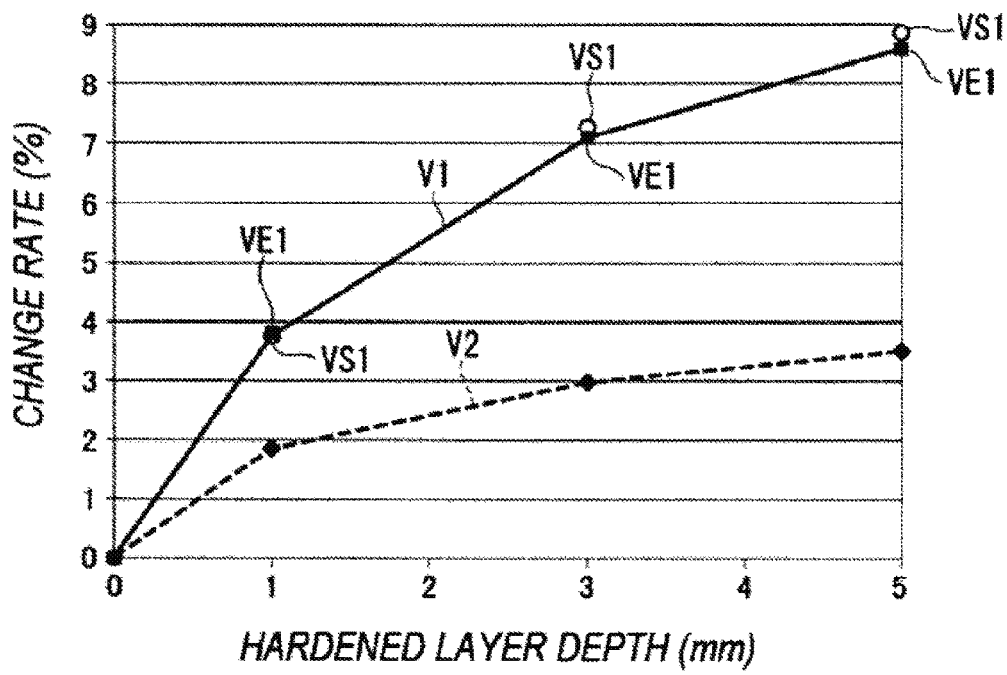
[Fig. 12]
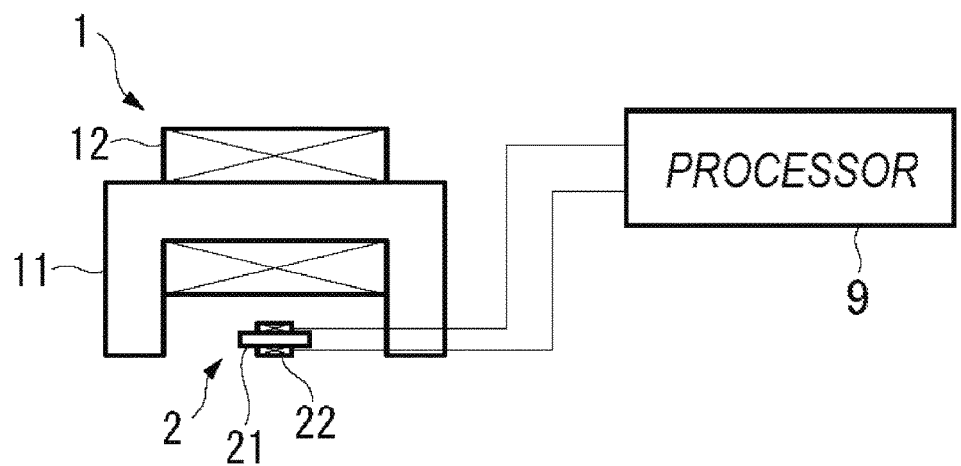

HARDENED LAYER DEPTH MEASURING APPARATUS

TECHNICAL FIELD

The present invention relates to a hardened layer depth measuring apparatus that measures the depth of a hardened layer formed at a surface layer of a quenched workpiece.

BACKGROUND ART

To improve metal strength, a workpiece such as a steel workpiece is hardened by performing an induction hardening. The induction hardening involves a quenching of a workpiece, forming a hardened layer at the surface of the workpiece. Mechanical characteristics varies depending on the depth of the hardened layer. Thus, quenching is performed under preset conditions, and a quality check is conducted after the production.

Conventionally, a workpiece is randomly selected and cut to check whether a quenching is properly being performed. However, with this method, not only the checking work takes time but also the workpiece selected for the checking work cannot later be used as a product.

According to a related art, an apparatus is provided to measure a depth of a hardened surface layer of a workpiece. The apparatus includes a magnetizer to magnetize the workpiece, a detecting coil to detect an induction magnetic field generated by the magnetizer, and quenching depth determining means for deriving the quenching depth of the workpiece from the output voltage value of the detecting coil and already-known information on magnetic characteristics of a material equivalent to the workpiece (see, e.g., WO2012/057224A1). The magnetizer has a U-shaped yoke, an excitation coil wound on a portion of the yoke that faces the workpiece, and a detection coil provided at a lower portion of a leg of the yoke.

In this related art example, the yoke has pair of leg portions and a base portion coupling the leg portions t each other, and is arranged such that the open side of the U-shape faces the workpiece. When current is applied to the excitation coil provided on the base portion, the magnetic flux flows through one of the leg portion, the workpiece, the other leg portion and the base portion in this order, and with this magnetic flux, a spatial magnetic flux is generated on the surface layer of the workpiece. The detecting coil detects this spatial magnetic flux. However, because the detecting coil is provided on the leg portion of the yoke, not only the spatial magnetic flux but also the magnetic flux generated inside the yoke are detected, so that measurement accuracy may not be sufficient.

SUMMARY

It is an object of the present invention to provide a hardened layer depth measuring apparatus with improved measurement accuracy.

According to an aspect of the present invention, a hardened layer depth measuring apparatus is configured to measure a depth of a hardened layer formed at a surface layer of a quenched workpiece. The hardened layer depth measuring apparatus includes an exciting coil configured to generate a magnetic flux to magnetize the workpiece and a detecting coil configured to detect the magnetic flux generated by the exciting coil. The exciting coil has a U-shaped excitation core portion and an excitation coil portion wound on the excitation core portion. The excitation core portion is arranged such that distal ends of magnetic poles of the excitation core portion face the workpiece. The detecting coil has a detection core portion having layers of magnetic sheets and a detection coil wound on the detection core portion. The detection core portion is arranged between the magnetic poles of the excitation core portion and along a surface of the workpiece.

According to this hardened layer depth measuring apparatus, when current is applied to the excitation coil portion, a magnetic flux flows inside the U-shaped excitation core portion and the workpiece, and with this magnetic flux, a spatial magnetic flux is generated on the surface layer of the workpiece. The detecting coil detects leakage magnetic flux flowing in this space. The voltage detected by the detecting coil varies depending on the depth of the hardened layer formed at the surface layer of the workpiece, and based on this detected voltage, the depth of the hardened layer is measured.

Because the detecting coil having the detection core portion is arranged at a position separated away from the exciting coil, the measurement of the depth of the hardened layer is less affected by the magnetic flux flowing inside the U-shaped excitation core portion as compared with the related art apparatus, so that the measurement accuracy is improved.

The hardened layer depth measuring apparatus may include a holding member that holds the exciting coil and the detecting coil together. With this configuration, the exciting coil and the detecting coil are positioned by the holding member. Therefore, setting of the exciting coil and the detecting coil on the workpiece is facilitated.

The holding member may be made of a synthetic resin. With this configuration, the exciting coil and the detecting coil are set in the mold before the synthetic resin poured into the mold is cured, and are held together once the synthetic resin is cured. That is, the holding member can be easily formed only by pouring a molten synthetic resin into the mold. Further, the synthetic resin prevents a short-circuit or a disconnection of the excitation coil portion and the detection coil portion during use.

The holding member may have a positioning portion configured to position the holding member with respect to the workpiece. With this configuration, when the holding member is moved with the positioning portion being engaged with a portion of the workpiece, the exciting coil and the detecting coil move together with the holding member while maintaining their relative positions. That is, the exciting coil and the detecting coil move while maintaining appropriate positions with respect to the workpiece. Therefore, more accurate measurement can be performed.

The detection core portion may be arranged at a middle point between the leg portions (magnetic poles) of the excitation core portion. With this configuration, the detection core portion is at an equal distance away from the respective leg portions of the excitation core portion. Therefore, it is less affected by the magnetic flux generated in the excitation core portion.

BRIEF DESCRIPTION OF DRAWINGS

FIG. 1A is a front view of a hardened layer depth measuring apparatus according to an embodiment of the present invention.

FIG. 1B is a side view of the hardened layer depth measuring apparatus.

FIG. 2A is a diagram illustrating a flow of magnetic flux in the hardened layer depth measuring apparatus in a case in which a hardened layer is formed at a surface of a workpiece.

FIG. 2B is a diagram illustrating a flow of magnetic flux in the hardened layer depth measuring apparatus in a case in which the hardened layer is not formed at the surface layer of the workpiece.

FIG. 3A is a contour map of a magnetic field intensity distribution, illustrating a simulation result of the hardened layer depth measuring apparatus in a case in which a hardened layer is formed at a surface of a workpiece.

FIG. 3B is a contour map of a magnetic field intensity distribution, illustrating a simulation result of the hardened layer depth measuring apparatus in a case in which the hardened layer is not formed at the surface layer of the workpiece.

FIG. 4A is a magnetic flux density vector distribution map, illustrating a simulation result of the hardened layer depth measuring apparatus in a case in which a hardened layer is formed at a surface of a workpiece.

FIG. 4B is a magnetic flux density vector distribution map, illustrating a simulation result of the hardened layer depth measuring apparatus in a case in which the hardened layer is not formed at the surface layer of the workpiece.

FIG. 5 is a graph showing a relationship between the hardened layer depth and the change rate with a constant current.

FIG. 6 is a graph showing a relationship between the hardened layer depth and the change rate with a constant frequency.

FIG. 7 is a schematic view of a hardened layer depth measuring apparatus used in a test.

FIG. 8 is a schematic diagram of a testing apparatus.

FIG. 9 is a graph showing a relationship between the effective hardened layer depth and the charge rate obtained through the test.

FIG. 10 is a graph showing a relationship between the hardened layer depth and the detected voltage with the excitation condition of 0.5 A current and 20 Hz frequency.

FIG. 11 is a graph showing a relationship between the hardened layer depth and the change rate, for comparison between an embodiment of the present invention and he related art.

FIG.12 is a front view of a hardened layer depth measuring apparatus and connected processor.

DESCRIPTION OF EMBODIMENTS

Hereinafter, embodiments of the present invention will be described in detail with reference to the drawings.

In the description, "quenching" is a heat treatment in which a metal is rapidly cooled from a high-temperature state. In a narrow sense, it is a heat treatment in which steel is firstly heated until its metal structure becomes an austenite structure and then rapidly cooled to obtain a martensite structure. The purpose of the quenching is to improve abrasion resistance, tensile strength and fatigue strength by hardening the material. In a broad sense, quenching is a treatment in which a metal, not limited to steel, is rapidly cooled from a high-temperature state, and includes heat treatments such as a solution treatment applied to austenitic stainless steel, maraging steel and the like and a water toughening treatment applied to high manganese steel. Thus, examples of the workpiece to which the present invention relates include carbon steel, austenitic stainless steel, maraging steel, high manganese steel and the like.

FIG. 1A is a front view of a hardened layer depth measuring apparatus according to an embodiment of the present invention, and FIG. 1B is a side view of the hardened layer depth measuring apparatus. The hardened layer depth measuring apparatus shown in FIGS. 1A and 1B is configured to measure a depth of a hardened layer H formed at a surface layer of a quenched workpiece W, and includes an exciting coil 1 configured to generate a magnetic flux, a detecting coil 2 configured to detect the magnetic flux generated by the exciting coil 1, and a holding member 3 that holds the exciting coil 1 and the detecting coil 2 together.

The exciting coil 1 magnetizes the workpiece W, and has an excitation core portion 11 having a U shape in a front view and an excitation coil portion 12 provided on the excitation core portion 11. The excitation core portion 11 has a pair of leg portions 111 (magnetic poles) and a base portion 110 coupling the base end portions of the leg portions 111 to each other. The excitation core portion 11 is arranged such that distal end faces of the leg portions 111 face the workpiece W. The excitation core portion 11 is configured as layers of magnetic metal sheets, such as silicon steel sheets, each being U-shaped in a planar view. The excitation core portion 11 has, in the front view, a length "l" along the surface of the workpiece W, a height "m" in a direction perpendicular to the surface of the workpiece W, and a leg width "n" (the width of the leg portion 111). The excitation coil portion 12 is wound on the base portion 110, and is connected to a non-illustrated power supply device.

The detecting coil 2 has a detection core portion 21 disposed between the leg portions 111 of the excitation core portion 11 and a detection coil portion 22 wound on the detection core portion 21. The detection core portion 21 is configured as layers of magnetic metal sheets, such as silicon steel sheets, each being rectangular in a planar view. The detection core portion 21 has a rectangular parallelepiped shape having a dimension "a" in a direction perpendicular to the surface of the workpiece W, a dimension "b" in a direction along the surface of the workpiece W, and the dimension "c" in a direction along which the detection coil portion 22 is wound (a<c, b<c). The detection core portion 21 is arranged on the workpiece W at a middle point between the pair of leg portions 111 such that the longitudinal direction of the detection core portion 21 extends along the longitudinal direction of the base portion 110. The relative positions of the detecting coil 2 and the surface of the workpiece W are optional. It is preferable that the detecting coil 2 contacts the surface of the workpiece W. The detection coil portion 22 is wound along the longitudinal direction of the detection core portion 21, and is connected to a processor 9 (see FIG. 12).The processor calculates the depth of the hardened layer H of the workpiece W based on the voltage (signal) output from the detection coil portion 22.

The holding member 3 is configured such that a portion of the outer peripheral surface thereof conforms to the cross-sectional shape of the workpiece W. For example, in the present embodiment, the portion of the outer peripheral surface of the holding member 3 is formed in a tubular shape having a semicircular cross section. The excitation coil portion 12 is partially exposed from the surface of the holding member 3 forming the chord of the semicircle. The detecting coil 2 is arranged so as to be flush with the tangential line of a point on the arc surface of the holding member 3. The holding member 3 is made of a synthetic resin such as an epoxy resin. In the present embodiment, the holding member 3 has a positioning portion 3A configured to position the holding member 3 with respect to the workpiece W. The shape of the positioning portion 3A may be designed in association with the shape of the workpiece W. For example, the positioning portion 3A may be configured as a protrusion extending along the axial direction of the excitation coil portion 12.

Next, the basic idea of the measurement according to the present embodiment will be described with reference to FIGS. 2A and 2B. FIGS. 2A and 2B illustrate a flow of magnetic flux in the hardened layer depth measuring apparatus. In FIGS. 2A and 2B, the illustration of the holding member 3 is omitted.

FIG. 2A illustrates a case in which the hardened layer H is formed at the surface layer of the workpiece W. The hardened layer H of the workpiece W has low magnetic permeability than a non-hardened layer of the workpiece W. With the workpiece W having the hardened layer H at the surface, when current is applied to the excitation coil portion 12, a large magnetic flux M1 is generated along the U-shaped excitation core portion 11, and together with this magnetic flux M1, a magnetic flux M21 forming a closed loop is generated. The magnetic flux M21 is generated only in the hardened layer H having low magnetic permeability, and is smaller than the magnetic flux M1.

FIG. 2B illustrates a case in which no hardened layer is formed at the surface layer of the workpiece W. The magnetic permeability of the entire workpiece W including the surface layer of the workpiece W is uniform. With this workpiece W, when current is applied to the excitation coil portion 12, the large magnetic flux M1 is generated along the U-shaped excitation core portion 11, and together with this magnetic flux M1, a magnetic flux M22 forming a closed loop is generated. In the workpiece W, since there is no hardened layer H having low magnetic permeability, the magnetic flux M22 is larger than the magnetic flux M21.

Regardless of the presence of the hardened layer H, with the magnetic flux M1, a spatial magnetic flux (leakage magnetic flux) N1 is generated along the surface of the workpiece W. The spatial magnetic flux N1 is detected by the detecting coil 2. The spatial magnetic flux N1 is large with the workpiece W having the hardened layer H at the surface layer, and is small with the workpiece W that does not have the hardened layer H at the surface layer. That is, the magnitude of the spatial magnetic flux N1 changes according to the depth of the hardened layer H, and by detecting this by the detecting coil 2, the depth of the hardened layer H can be measured.

The measurement of the depth of the hardened layer H of the workpiece W using the hardened layer depth measuring apparatus of the present embodiment will be described based on a simulation.

Simulation Conditions
Workpiece W:
Four flat plates having different depths of hardened layers H are considered as workpiece W. The dimensions of the workpiece W are 230 mm in width and 20 mm in height. The depths of the hardened layers H are 0 mm, 1 mm, 3 mm and 5 mm, respectively.
Exciting Coil:
Excitation core portion: silicon steel plate
30 mm (dimension "l")×15 mm (dimension "m")
leg width "n": 5 mm
Excitation coil portion: 165 turns
Detecting Coil:
Detection core portion: silicon steel plate
Dimension "c": 8 mm
Dimension "a": 0.5 mm
Detection coil portion: 100 turns
Excitation Conditions: see Table 1

Magnetic Properties: see Table 2
Magnetic Property Distribution of Each Model: see Table 3
Analytical Method: magnetic field analysis software—JMAG-Designer, 2D frequency response analysis

TABLE 1

| | Excitation Current | | |
|---|---|---|---|
| Frequency | 0.25 A | 0.5 A | 0.75 A |
| 20 Hz | Performed | Performed | Performed |
| 50 Hz | Not performed | Performed | Not performed |
| 100 Hz | Not performed | Performed | Not performed |
| 150 Hz | Not performed | Performed | Not performed |

TABLE 2

| | Carbon Steel | | Intra-JMAG |
|---|---|---|---|
| Material | no hardened layer (unquenched) | with hardened layer (quenched) | Data Magnetic Steel Sheet 20HX1300 |
| Maximum Relative Permeability | 427 | 187 | — |
| Conductivity (S/m) | $3.79 \times 10^6$ | $4.95 \times 10^6$ | $1.85 \times 1.0^6$ |

TABLE 3

| Flat Plate Workpiece | 0 mm Depth Model | 1 mm Depth Model | 3 mm Depth Model | 5 mm Depth Model |
|---|---|---|---|---|
| Hardened Layer 1.0 mm | no hardened layer | with hardened layer | with hardened layer | with hardened layer |
| Hardened Layer 3.0 mm | no hardened layer | no hardened layer | with hardened layer | with hardened layer |
| Hardened Layer 5.0 min | no hardened layer | no hardened layer | no hardened layer | with hardened layer |

The results of the simulation performed under the above conditions are shown as contour maps in FIGS. 3A and 3B. FIGS. 3A and 3B show the results of the simulation conducted with the frequency of 20 Hz and the excitation current of 0.25 A.

As shown in FIG. 3A, in the workpiece W with the depth of the hardened layer H being 5 mm, a magnetic flux G1 of a large magnetic field is generated around the leg portions 111 of the excitation core portion 11 and around both end portions of the detection core portion 21. A magnetic flux G2 of a magnetic field smaller than that of the magnetic flux G1 is generated and a magnetic flux G3 of a magnetic field smaller than that of the magnetic flux G2 is generated to surround the magnetic flux G1.

In contrast, as shown in FIG. 3B, in the unquenched workpiece W with no hardened layer, while the areas around of the leg portions 111 of the excitation core portion 11 are the same as in FIG. 3A, the magnetic flux generated around both end portions of the detection core portion 21 is the magnetic flux G2, the magnetic field of which being smaller than that of the magnetic flux G1.

That is, the magnetic field generated around both end portions of the detection core portion 21 is large in the quenched workpiece W having the hardened layer H as compared with in the unquenched workpiece W with no hardened layer.

FIGS. 4A and 4B illustrate magnetic flux density vector distributions from the simulation results of the hardened layer depth measuring apparatus. FIGS. 4A and 4B show the results of the simulation conducted with the frequency of 20 Hz and the excitation current of 0.25 A.

FIG. 4A illustrates a case in which a hardened layer is formed at the surface layer of the workpiece, and FIG. 4B illustrates a case in which no hardened layer is formed at the surface layer of the workpiece. Comparing FIGS. 4A and 4B, while magnetic fluxes concentrate around both ends of the detection core portion 21 in both cases, the magnetic flux density is higher in the workpiece W having the hardened layer H than in the workpiece W with no hardened layer. This is considered to be because more magnetic flux leaks into the air from the quenched workpiece W having the hardened layer H than from the unquenched workpiece W with no hardened layer.

The above simulation results show that the hardened layer depth measuring apparatus of the present embodiment can measure the depth of the hardened layer as the detection voltage will change depending on the depth of the hardened layer.

FIG. 5 shows a relationship between the hardened layer depth and the change rate with a constant current. In FIG. 5, the change rate is the rate of the detection voltage with reference to the unquenched workpiece having no hardened layer.

As shown in FIG. 5, the change rate P1 with the frequency of 20 Hz substantially linearly ascends with constant inclination when the hardened layer depth increases from 0 mm to 3.0 mm, and still ascends when the hardened layer depth further increases although the inclination decreases. In contrast, regarding the change rate P2 with the frequency of 50 Hz, the change rate P3 with the frequency of 100 Hz and the change rate P4 with the frequency of 150 Hz, the inclination decreases before the hardened layer depth becomes 3.0 mm as compared with the change rate P1, and when the hardened layer depth exceeds 3.0 mm, the inclination becomes minus.

FIG. 6 shows a relationship between the hardened layer depth and the change rate with a constant frequency. In FIG. 6, the change rate Q1 when the current is 0.25 A is such that the change rate is the same when the hardened layer depth is 0 to 3.0 mm and substantially linearly ascends and then, ascends although the inclination decreases. On the contrary, regarding the change rate Q2 when the current is 0.5 A and the change rate Q3 when it is 0.75 A, compared with the change rate Q1, the inclination decreases before the hardened layer depth becomes 3.0 mm.

Generally, to improve the detection accuracy, it is preferable that the detection voltage and the hardened layer depth are in a proportional relationship in that the detection voltage linearly increases as the hardened layer depth increases. When the relationship between the detection voltage and the hardened layer depth includes a proportional relationship as described above, the hardened layer depth can be separated from the detection voltage. On the contrary, when the detection voltage does not change even if the hardened layer depth increases and when the detection voltage decreases if the hardened layer depth increases, the hardened layer depth cannot be separated from the detection voltage.

From FIG. 5 and FIG. 6, it is found that, among the excitation conditions, the frequency of 20 Hz and the current of 0.25 A is the most suitable condition for the measurement of the hardened layer depth.

The measurement of the depth of the hardened layer H of the workpiece W using the hardened layer depth measuring apparatus of the present embodiment will be described based on a test.

In the test, a plurality of workpieces W with different depths of the hardened layers H were prepared, and on these, the detection voltage was detected by the hardened layer depth measuring apparatus.

FIG. 7 shows a condition where the hardened layer depth measuring apparatus used in the test is attached to the workpiece W. In FIG. 7, the workpiece W used in the test is a grooved workpiece, and the cross-sectional shape thereof has a substantially semicircular inner peripheral surface. A concave guide groove WG is provided on a straight line WL passing through the circle center O and perpendicular to the chord on the semicircular inner peripheral surface. In the present test, two positions B and C each separated by an angle α (45°) from a straight line L connecting the circle center O and the guide groove WG are the measurement positions.

Workpiece W
Workpiece: grooved workpiece
Material: carbon steel
Hardness limit: 446 HV
Workpiece variation: four patterns—no hardened layer (unquenched), shallow hardened layer H, normal-depth hardened layer H, and deep hardened layer H
Specifications of Effective Hardened Layer Depth:
Workpiece W with shallow hardened layer H—effective hardened layer depth being 3.15 mm at point B and 2.71 mm at point C
Workpiece W with normal-depth hardened layer H—effective hardened layer depth being 3.25 mm at point B and 3.04 mm at point C
Workpiece W with deep hardened layer H—effective hardened layer depth being 3.77 mm at point B and 3.74 mm at point C
The effective hardened layer depth is a depth from the surface to a point of hardness limit.

Hardened Layer Depth Measuring Apparatus
Excitation Core Portion 11
Dimensions of single silicon steel sheet: l=30 mm, m=15 mm, n=5 mm, thickness t=0.2 mm
Twenty five layers of silicon steel sheets forming the excitation core portion 11 (the overall thickness of the core being 5 mm)
Excitation Coil Portion 12: 165 turns of 0.45 mm diameter wire
Detection Core Portion 21:
Dimensions of single silicon steel sheet: c=7.5 mm, b=1.5 mm, thickness t=0.2 mm
Four layers of silicon steel sheets forming the detection core portion 21 (the overall thickness (dimension "a") of the core being 0.8 mm).
Detection Coil Portion 22: 100 turns of 0.07 mm diameter wire
Holding Member 3
Material: Epoxy Resin
Molding method: The actual workpiece W is used as a mold. Epoxy resin is poured into the mold. Before the epoxy resin is cured, the exciting coil 1 and the detecting coil 2 after winding are embedded. Then, the epoxy resin is cured.

Testing Apparatus
FIG. 8 is a schematic diagram of the testing apparatus. In FIG. 8, the holding member 3 of the hardened layer depth measuring apparatus is omitted. As shown in FIG. 8, a resistor 4 and a bipolar power supply 5 are connected to the exciting coil 1 of the hardened layer depth measuring apparatus, and a frequency generator 6 is connected to the bipolar power supply 5. A signal amplifier 7 is connected to the detecting coil 2 of the hardened layer depth measuring apparatus. An oscilloscope 8 is connected to the resistor 4 and the signal amplifier 7.

Resistor 4: 1Ω resistor made by parallel-connected twenty two metal film resistances of ¼W 22Ω

Bipolar Power Supply 5: Four-Quadrant Bipolar Power Supply (BWS40-7.5) manufactured by Takasago Ltd.

Frequency Generator 6: Function Generator DF1906 manufactured by NF corporation Signal Amplifier 7: Isolation Amplifier 5325 manufactured by NF corporation Oscilloscope 8: Oscilloscope TDS3054B manufactured by Tektronix, Inc.

Measurement Method

Excitation is performed according to the excitation conditions shown in Table 4, and the effective value of the detection voltage waveform output from the detecting coil 2 is read by the oscilloscope 8. Since the detection voltage waveform was minute, the amplification factor at the signal amplifier 7 was 200 times.

TABLE 4

| Frequency | Excitation Current | | |
|---|---|---|---|
| | 0.25 A | 0.5 A | 0.75 A |
| 20 Hz | Performed | Performed | Performed |
| 50 Hz | Not performed | Performed | Not performed |
| 100 Hz | Not performed | Performed | Not performed |

Test Results

FIG. 9 is a graph showing a relationship between the effective hardened layer depth and the charge rate obtained by the test. The change rate of FIG. 9 is the rate of the detection voltage with reference to the unquenched workpiece having no hardened layer.

In FIG. 9, R1 is the change rate when the excitation current is 0.25 A and the frequency is 20 Hz, R2 is the change rate when the excitation current is 0.5 A and the frequency is 20 Hz, R3 is the change rate when the excitation current is 0.75 A and the frequency is 20 Hz, R4 is the change rate when the excitation current is 0.5 A and the frequency is 50 Hz, and R5 is the change rate when the excitation current is 0.5 A and the frequency is 100 Hz. From these change rates R1 to R5, it is found that the detection voltage tends to increase as the effective hardened layer depth increases.

The $R^2$ value indicating the correlation between the effective hardened layer depth and the detection voltage is 0.973 when the excitation current is 0.25 A and the frequency is 20 Hz, is 0.9983 when the excitation current is 0.5 A and the frequency is 20 Hz, is 0.9908 when the excitation current is 0.75 A and the frequency is 20 Hz, is 0.9878 when the excitation current is 0.5 A and the frequency is 50 Hz, and is 0.9721 when the excitation current is 0.5 A and the frequency is 100 Hz. From these pieces of data, it was found that the $R^2$ value indicating the correlation between the effective hardened layer depth and the detection voltage is highest when the current is 0.5 A and the frequency is 20 Hz.

FIG. 10 is a graph showing a relationship between the hardened layer depth and the detection voltage when the excitation condition is that the current is 0.5 A and the frequency is 20 Hz, and a measurement variation error (n=5) is shown. In FIG. 10, the line S1 indicates the test result, and the line S2 indicates the approximate straight line.

In the measurement of the present test, the maximum variation width d was approximately 0.2 mm in the measurement of the position B of the workpiece W having the normal-depth hardened layer H.

From the above test results, it was found that while a correct detection voltage was not obtained because of a large noise component under the appropriate excitation condition (the current is 0.25 A and the frequency is 20 Hz) confirmed by the simulation, the effective hardened layer depth could be measured with a maximum variation width "d" of approximately 0.2 mm under an excitation condition where the current was 0.5 A and the frequency was 20 Hz.

The above-described embodiment of the present invention is advantageous in the following aspects:

(1) The detecting coil 2 has the detection core portion 21 arranged on the workpiece W and between the leg portions 111 of the excitation core portion 11 and the detection coil portion 22 wound on the detection core portion 21. That is, the detecting coil 2 is arranged at a position separated away from the exciting coil 1, and is less likely to be affected by the magnetic flux flowing through the excitation core portion 11. Therefore, the measurement accuracy is improved as compared with the related art example.

The graph of FIG. 11 shows this advantage of the present embodiment. FIG. 11 shows relationships between the hardened layer depth and the change rate, according to the present embodiment and the related art example disclosed in WO2012/057224A1. In FIG. 11, the change rate V1 of the present embodiment is obtained by a test similar to the test described above. The simulation result VS1 of the present embodiment is in a position approximate to the test result VE1. The change rate V2 of the related art example is the one obtained by a test similar to the test of the present embodiment. As shown in FIG. 11, the change rate V1 of the present invention is higher than the change rate V2 of the related art example. A high change rate indicates high detection accuracy.

(2) The exciting coil 1 and the detecting coil 2 are joined together by the holding member 3. That is, the exciting coil 1 and the detecting coil 2 are positioned by the holding member 3, so that the setting the exciting coil 1 and the detecting coil 2 on the workpiece W is facilitated. Further, since measurement can be performed in a state in which the exciting coil 1 and the detecting coil 2 are positioned, the measurement accuracy can be prevented from being lowered.

(3) The holding member 3 is made of a synthetic resin such as epoxy resin. Therefore, the holding member 3 can be easily formed only by pouring a molten synthetic resin into a mold. Because the excitation coil portion 12 and the detection coil portion 22 are fixed in this holding member 3, short-circuit or disconnection during use is prevented.

(4) The holding member 3 has the positioning portion 3A that positions the holding member 3 with respect to the workpiece W. Therefore, the exciting coil 1 and the detecting coil 2 move while maintaining appropriate positions with respect to the workpiece W, so that more accurate measurement can be performed.

(5) The detection core portion 21 is arranged at the middle point between the leg portions 111 of the excitation core portion 11. That is, the detection core portion 21 is at an equal distance away from the pair of leg portions 111 of the excitation core portion 11. Therefore, it is less affected by the magnetic flux generated in the excitation core portion 11, so that the measurement accuracy is further improved.

While the present invention has been described with reference to certain exemplary embodiments thereof, the scope of the present invention is not limited to the embodiments described above, and it will be understood by those skilled in the art that various changes and modifications may be made therein without departing from the scope of the present invention as defined by the appended claims.

For example, while the holding member 3 has the positioning portion 3A for positioning the holding member 3 with respect to the workpiece W in the embodiment described above, the positioning portion 3A may not be provided.

Further, the holding member 3 itself is may not be provided to implement the present invention. Even if the holding member 3 is provided, the present invention is not limited to the structure of the embodiment described above. For example, the shape of the holding member 3 is not limited to the shape of the embodiment described above, and may be a rectangular parallelepiped, a cylinder, a triangular prism or the like. The holding member 3 may be configured such that the exciting coil 1 and the detecting coil 2 are fixed to a base.

In assembling the hardened layer depth measuring apparatus, while a synthetic resin such as epoxy resin is injected into the workpiece W and then the exciting coil 1 and the detecting coil 2 are embedded in the embodiment described above, a synthetic resin may be injected after the exciting coil 1 and the detecting coil 2 are set on the workpiece W, or a synthetic resin may be injected into a separately prepared mold instead of the workpiece W.

This application is based on Japanese Patent Application No. 2015-045307 filed on Mar. 6, 2015, the entire content of which is incorporated herein by reference.

The invention claimed is:

1. A hardened layer depth measuring apparatus configured to measure a depth of a hardened layer formed at a surface layer of a quenched workpiece, the hardened layer depth measuring apparatus comprising:
an exciting coil configured to generate a magnetic flux to magnetize the workpiece responsive to an alternating excitation current output by a power supply;
a detecting coil configured to detect the magnetic flux generated by the exciting coil; and
a processor,
wherein the exciting coil comprises a U-shaped excitation core portion and an excitation coil portion wound on the excitation core portion, the excitation core portion being arranged such that distal ends of magnetic poles of the excitation core portion face the workpiece, and
wherein the detecting coil comprises a detection core portion having layers of magnetic sheets and a detection coil wound on the detection core portion, the detection core portion being arranged between the magnetic poles of the excitation core portion and along a surface of the workpiece,
wherein the detection core portion is connected to the processor, the processor being configured to calculate the depth of the hardened layer based on a detection voltage output from the detection core portion and a predetermined correlation between hardened layer depth values and detection voltage values, and
wherein a current value and a frequency value of the excitation current are selected such that the detection voltage is approximately proportional to the depth of the hardened layer.

2. The hardened layer depth measuring apparatus according to claim 1, further comprising a holding member that holds the exciting coil and the detecting coil together.

3. The hardened layer depth measuring apparatus according to claim 2, wherein the holding member is made of a synthetic resin.

4. The hardened layer depth measuring apparatus according to claim 2, wherein the holding member comprises a positioning portion configured to position the holding member with respect to the workpiece.

5. The hardened layer depth measuring apparatus according to claim 1, wherein the detection core portion is arranged at a middle point between the magnetic poles of the excitation core portion.

6. The hardened layer depth measuring apparatus according to claim 1, wherein the processor is configured to calculate the depth of the hardened layer based on a change rate of the detection voltage with reference to an unquenched workpiece having no hardened layer.

7. The hardened layer depth measuring apparatus according to claim 1, wherein the detecting coil is arranged at a position separated away from the exciting coil.

8. The hardened layer depth measuring apparatus according to claim 1, wherein the detecting coil is not in direct contact with the exciting coil.

9. The hardened layer depth measuring apparatus according to claim 1, wherein the excitation core portion comprises a pair of leg portions and a base portion coupling base end portions of the leg portions to each other, and
wherein the detection core portion is arranged such that a longitudinal direction of the detection core portion extends along a longitudinal direction of the base portion.

* * * * *